US010596041B2

(12) United States Patent
Allred (10) Patent No.: US 10,596,041 B2
(45) Date of Patent: Mar. 24, 2020

(54) APPARATUSES AND METHODS FOR MINIMIZING WOUND DEHISCENCE, SCAR SPREAD, AND/OR THE LIKE

(71) Applicant: Seton Healthcare Family, Austin, TX (US)

(72) Inventor: James Allred, Austin, TX (US)

(73) Assignee: ASCENSION TEXAS, Austin, TX (US)

( * ) Notice: Subject to any disclaimer, the term of this patent is extended or adjusted under 35 U.S.C. 154(b) by 216 days.

(21) Appl. No.: 14/663,833

(22) Filed: Mar. 20, 2015

(65) Prior Publication Data

US 2016/0058622 A1    Mar. 3, 2016

Related U.S. Application Data

(60) Provisional application No. 62/043,012, filed on Aug. 28, 2014.

(51) Int. Cl.
*A61F 13/00* (2006.01)
*A61F 13/02* (2006.01)

(52) U.S. Cl.
CPC .... *A61F 13/0233* (2013.01); *A61F 13/00063* (2013.01); *A61F 2013/0028* (2013.01);
(Continued)

(58) Field of Classification Search
CPC ............ A61F 13/0233; A61F 13/00063; A61F 13/00025; A61F 13/00038; A61F 13/0243;
(Continued)

(56) References Cited

U.S. PATENT DOCUMENTS 1,969,188 A * 8/1934 Spicer ................. A61B 17/085
606/216
3,026,874 A    3/1962 Stevens ......................... 604/305
(Continued)

FOREIGN PATENT DOCUMENTS

EP         2599446       6/2013
WO    WO 9424972 A1 * 11/1994 ........... A61F 13/023

OTHER PUBLICATIONS

Material Safety Data Sheet, VELCRO Brand Hook 88 and Loop 1000 with Holt Melt Pressure Sensitive Adhesive, Velcro USA Inc., Aug. 2, 2012.*
(Continued)

*Primary Examiner* — Kim M Lewis
(74) *Attorney, Agent, or Firm* — Norton Rose Fulbright US LLP (57) ABSTRACT

Apparatuses for minimizing scar spread and reducing risk of wound dehiscence and related methods. Some of the apparatuses include a flexible first strip and a flexible second strip, the first and second strips configured to be coupled to a patient's back on opposing sides of a wound and a substantially inelastic and flexible layer of material configured to be directly coupled to the first and second strips with the layer in tension to resist separation of the first and second strips, where the layer is configured to be removably coupled to at least one of the first and second strips. In some of the apparatuses, the layer is configured to be removably coupled to each of the first and second strips. In some of the apparatuses, the layer is non-removably coupled to and/or is unitary with at least one of the first and second strips.

19 Claims, 4 Drawing Sheets

(52) U.S. Cl.
CPC ........... *A61F 2013/00165* (2013.01); *A61F 2013/00217* (2013.01); *A61F 2013/00289* (2013.01)

(58) Field of Classification Search
CPC ........ A61F 13/0246; A61F 2013/00165; A61F 2013/00106; A61F 2013/00855; A61F 2013/00868; A61F 2013/00374; A61F 2013/00361; A61F 2013/00307; A61F 2013/00089; A61B 17/085; A61L 15/58; A61L 24/046; A61L 27/18; A61L 15/28; A61L 24/08; A61L 26/0052; A61L 31/042; A61L 24/0042; A61L 15/26; A61L 24/001; A61L 15/225; A61L 24/0036; A61L 24/0015; A61L 24/0031; A61L 24/06; A61L 31/148; A61L 31/16; A61L 15/425; A61L 2300/406; A61L 26/0023; A61L 15/44; A61L 2400/04; A61L 2400/16; A61L 24/043; A61L 26/0019; A61L 26/008; A61L 26/0085; A61L 27/26; A61L 27/52; A61L 27/56; A61L 15/24; A61L 15/64; A61L 27/3629; A61L 31/14; A61L 2300/802; A61L 2430/00; A61L 15/325; A61L 15/38; A61L 15/40; A61L 15/42; A61L 2300/104; A61L 2300/404; A61L 2300/604; A61L 2400/18; A61L 26/0076; A61L 27/24; A61L 27/3641; A61L 27/3683; A61L 27/3687; A61L 27/54; A61L 2/025; A61L 2/24; A61L 31/005; A61L 31/045; A61L 31/047; A61L 31/128; A61L 15/18; A61L 15/585; A61L 2300/102; A61L 2300/252; A61L 2300/418; A61L 2300/432; A61L 24/0094; A61L 24/04; A61L 24/102; A61L 24/106; A61L 24/108; A61L 26/0042; A61L 26/0057; A61L 26/0066; A61L 27/225; A61L 27/227; A61L 27/40; A61L 27/48

USPC ......................................................... 606/216
See application file for complete search history.

(56) References Cited

U.S. PATENT DOCUMENTS

| | | | | |
|---|---|---|---|---|
| 3,698,395 A * | 10/1972 | Hasson | ................ | A61B 17/085 602/58 |
| 4,212,296 A | 7/1980 | Schaar | ............................ | 602/42 |
| 4,709,695 A | 12/1987 | Kohn et al. | .................... | 128/858 |
| 4,825,866 A * | 5/1989 | Pierce | .................. | A61B 17/085 606/216 |
| 5,086,763 A | 2/1992 | Hathman | ........................ | 602/42 |
| 5,149,331 A | 9/1992 | Ferdman et al. | ............. | 604/290 |
| 5,176,703 A * | 1/1993 | Peterson | .............. | A61B 17/085 602/41 |
| 5,234,462 A * | 8/1993 | Pavletic | ................ | A61B 17/085 606/215 |
| 5,263,970 A * | 11/1993 | Preller | ................ | A61B 17/085 602/58 |
| 5,336,219 A * | 8/1994 | Krantz | ................ | A61B 17/085 606/213 |
| 5,718,695 A | 2/1998 | Keegan et al. | ................ | 604/290 |
| 5,947,914 A | 9/1999 | Augustine | ........................ | 602/2 |
| 5,954,680 A | 9/1999 | Augustine | ........................ | 602/42 |
| 5,964,721 A | 10/1999 | Augustine | ........................ | 602/2 |
| 5,964,723 A | 10/1999 | Augustine | ........................ | 602/42 |
| 6,013,097 A | 1/2000 | Augustine et al. | ............. | 607/96 |
| 6,045,518 A | 4/2000 | Augustine | ........................ | 602/2 |
| 6,071,254 A | 6/2000 | Augustine | ........................ | 602/2 |
| 6,093,160 A | 7/2000 | Augustine et al. | ............. | 602/2 |
| 6,110,197 A | 8/2000 | Augustine et al. | ........... | 607/108 |
| 6,113,561 A | 9/2000 | Augustine | ........................ | 602/2 |
| 6,164,279 A | 12/2000 | Tweedle | ........................ | 128/888 |
| 6,217,535 B1 | 4/2001 | Augustine | ........................ | 602/2 |
| 6,241,697 B1 | 6/2001 | Augustine | ........................ | 602/2 |
| 6,241,698 B1 | 6/2001 | Augustine | ........................ | 602/2 |
| 6,264,622 B1 | 7/2001 | Augustine | ........................ | 602/2 |
| 6,267,740 B1 | 7/2001 | Augustine et al. | ............. | 602/2 |
| 6,293,917 B1 | 9/2001 | Augustine et al. | ............. | 602/2 |
| 6,402,724 B1 | 6/2002 | Smith et al. | .................. | 604/289 |
| 6,406,448 B1 | 6/2002 | Augustine | ........................ | 602/2 |
| 6,407,307 B1 | 6/2002 | Augustine | ........................ | 602/42 |
| 6,419,651 B1 | 7/2002 | Augustine | ........................ | 602/2 |
| 6,423,018 B1 | 7/2002 | Augustine | ........................ | 602/2 |
| 706,250 A1 | 8/2002 | Muller | ........................ | 128/888 |
| 6,458,109 B1 | 10/2002 | Henley et al. | ................ | 604/304 |
| 6,987,209 B2 | 1/2006 | Augustine et al. | ............. | 602/42 |
| 7,122,712 B2 * | 10/2006 | Lutri | .................... | A61F 13/0216 602/43 |
| 7,166,760 B1 * | 1/2007 | Talbot | ................... | A61F 13/066 602/23 |
| 7,332,641 B2 * | 2/2008 | Lebner | ................ | A61B 17/085 602/41 |
| 7,622,629 B2 | 11/2009 | Aali | ................................ | 602/58 |
| 7,745,683 B2 | 6/2010 | Aali | ................................ | 602/58 |
| 7,928,281 B2 | 4/2011 | Augustine | ........................ | 602/48 |
| 7,981,136 B2 * | 7/2011 | Weiser | ................. | A61B 17/085 602/42 |
| 8,021,347 B2 | 9/2011 | Vitaris et al. | .................. | 604/304 |
| 8,063,263 B2 * | 11/2011 | Gurtner | .................. | A61K 47/67 523/111 |
| 8,105,353 B2 * | 1/2012 | Lebner | ................ | A61B 17/085 606/213 |
| 8,227,657 B2 | 7/2012 | Aali | ................................ | 602/58 |
| 8,764,792 B2 * | 7/2014 | Weiser | ................. | A61B 17/085 602/42 |
| 2003/0092969 A1 * | 5/2003 | O'Malley | .............. | A61B 17/02 600/216 |
| 2004/0193216 A1 * | 9/2004 | Deutsch | ................ | A61B 17/085 606/216 |
| 2008/0108924 A1 * | 5/2008 | Molan | ................... | A61F 13/023 602/48 |
| 2011/0046669 A1 | 2/2011 | Goraltchouk et al. | ........ | 606/228 |
| 2012/0310132 A1 | 12/2012 | Hirashima | ...................... | 602/43 |
| 2017/0189240 A1 * | 7/2017 | Zepeda | .............. | A61F 13/0236 |

OTHER PUBLICATIONS

Material Safety Data Sheet, Velcro Brand Hook, Velcro USA (Year: 2007).*

* cited by examiner

APPARATUSES AND METHODS FOR MINIMIZING WOUND DEHISCENCE, SCAR SPREAD, AND/OR THE LIKE

CROSS-REFERENCE TO RELATED APPLICATIONS

This application claims priority to U.S. Provisional Patent Application No. 62/043,012 filed Aug. 28, 2014, which is incorporated by reference in its entirety.

BACKGROUND

1. Field of Invention

The present invention relates generally to wound care, and more specifically, but not by way of limitation, to apparatuses and methods for minimizing wound dehiscence, scar spread, and/or the like.

2. Description of Related Art

Wound dehiscence may be a relatively common surgical complication and typically occurs when a closed surgical incision breaks open or splits. For example, in a typical healing process, sutures or closures surrounding and/or closing a wound stay intact while new tissue (e.g., granulation tissue) forms between and/or across the wound edges. However, when wound dehiscence occurs, the wound edges can separate, and the wound can open or split along the sutures or closures. In the event of wound dehiscence, further surgical treatment is generally required (e.g., to treat and reclose the wound). Patients who are diabetic, obese, aged, and/or the like, or patients with relatively large or wide incisions, such as elliptical incisions, may be at an increased risk of wound dehiscence.

To mitigate the risk of wound dehiscence, some surgeons may attempt to pucker the skin around the wound during suturing. However, as the wound heals and a scar forms, the puckered and/or scar tissue may begin to flatten and spread (e.g., due to the relatively low tensile strength of such tissue).

Generally, scar spread results when a post-surgical scar widens over time. Scar tissue in high-tension areas, such as on a patient's back, shoulders, thighs, and/or the like, can be at an increased risk of spreading. Scar spread can occur long after a wound has healed, and in some instances, may not manifest until weeks or months after a wound has healed and/or the patient has completed follow-up treatments.

Although the skin and scar typically remain intact during scar spread, scar spread is nevertheless a serious dermatological problem. For example, large scars (e.g., due at least in part to size and/or appearance) are a common complaint of patients and may lead to patient dissatisfaction and distrust in the treating clinician.

Current devices designed to minimize wound dehiscence and/or scar spread can include sterile strips or skin adhesive. However, these devices can impose limitations for both the patient and the clinician. For example, a clinician may not be able to adequately examine, clean, and/or treat the wound during healing without removing the sterile strips or skin adhesive, and once these devices are removed, they must typically be disposed of and replaced. Additionally, these devices may hinder other wound treatments, such as the application of medicaments (e.g., antibiotics or therapeutics) to the wound.

Examples of wound enclosures are disclosed in U.S. Pat. No. 4,709,695.

SUMMARY

Some embodiments of the present wound care apparatuses are configured, through a substantially inelastic and flexible layer of material configured to be directly coupled to flexible first and second strips coupled to a patient's skin on opposing sides of a wound, to pucker and/or apply compression to the wound to minimize wound dehiscence, scar spread, and/or the like.

Some embodiments are configured, through a removable coupling (e.g., via hook-and-loop fasteners, adhesive, and/or the like) between the substantially inelastic and flexible layer of material and at least one of the flexible first and second strips, to allow a clinician to remove the layer to examine, clean, treat, and/or medicate the wound, and/or adjust the pucker and/or compression applied to the wound. Some embodiments are configured, through a recouplable coupling between the substantially inelastic and flexible layer of material and at least one of the flexible first and second strips, to achieve such desirable functionality without requiring replacement of the apparatus, strips, layer, and/or the like.

Some embodiments are configured, through a maximum thickness of the wound care apparatus that is substantially equal to a thickness of the flexible first or second strip plus a thickness of the inelastic and flexible layer of material, to allow the apparatus to be discretely worn by a patient (e.g., under a patient's clothing).

Thus, the present wound care apparatuses and methods can provide a discrete and effective approach to minimizing wound dehiscence, scar spread, and/or the like, while still allowing for observation, cleaning, treatment, and/or the like during the wound healing process.

Some of the present apparatuses for minimizing scar spread and reducing risk of wound dehiscence comprise a flexible first strip, a flexible second strip, the first and second strips configured to be coupled to a patient's skin on opposing sides of a wound, and a substantially inelastic and flexible layer of material configured to be directly coupled to the first and second strips with the layer in tension to resist separation of the first and second strips, where the layer is configured to be removably coupled to at least one of the first and second strips. In some embodiments, the apparatus has a maximum thickness that is substantially equal a thickness of the first or second strip plus a thickness of the layer. In some embodiments, the layer comprises an absorbent pad.

In some embodiments, the layer is configured to be removably coupled to each of the first and second strips. In some embodiments, the layer is non-removably coupled to at least one of the first and second strips. In some embodiments, the layer is unitary with at least one of the first and second strips.

In some embodiments, the first and second strips comprise adhesive. In some embodiments, the layer comprises adhesive. In some embodiments, the layer and at least one of the first and second strips comprise hook-and-loop fasteners. In some embodiments, the apparatus is configured such that the layer can be removed from at least one of the first and second strips without removing the first and second strips from the patient's skin. In some embodiments, the layer is configured to be recoupled to at least one of the first and second strips after the layer has been removed from the at least one strip.

Some embodiments of the present methods for minimizing scar spread and reducing risk of wound dehiscence comprise coupling a flexible first strip and a flexible second strip to a patient's skin on opposing sides of a wound and coupling a substantially inelastic and flexible layer of material across the first and second strips such that the layer is held in tension by the first and second strips. In some embodiments, the layer is directly and removably coupled to at least one of the first and second strips. Some embodiments comprise removing the layer from at least one of the first and second strips without removing the first and second strips from the patient's skin. Some embodiments comprise recoupling the layer across the first and second strips such that the layer is held in tension by and resists separation of the first and second strips. Some embodiments comprise trimming at least one of the first strip, second strip, and layer.

Some embodiments of the present methods for minimizing scar spread and reducing risk of wound dehiscence comprise adjusting a distance between a flexible first strip and a flexible second strip, the first and second strips coupled to a patient's skin on opposing sides of a wound, and coupling an inelastic and flexible layer of material across the first and second strips such that the layer is held in tension by and resists separation of the first and second strips. In some embodiments, the coupling of the layer to at least one of the first and second strips is removable and direct.

Some embodiments of the present methods for providing access to a wound comprise releasing a substantially inelastic and flexible layer of material from a direct coupling with at least one of a flexible first strip and a flexible second strip in which the layer is under tension between the first and second strips, where the first and second strips remain coupled to a patient's skin on opposing sides of the wound.

Some embodiments of the present methods comprise applying a medicament to the wound. In some embodiments, at least a portion of the wound is on the patient's back. In some embodiments, at least a portion of the wound is on the patient's thigh.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, 10, and 20 percent.

Further, an apparatus or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

DETAILED DESCRIPTION OF ILLUSTRATIVE EMBODIMENTS

Figure 1A:
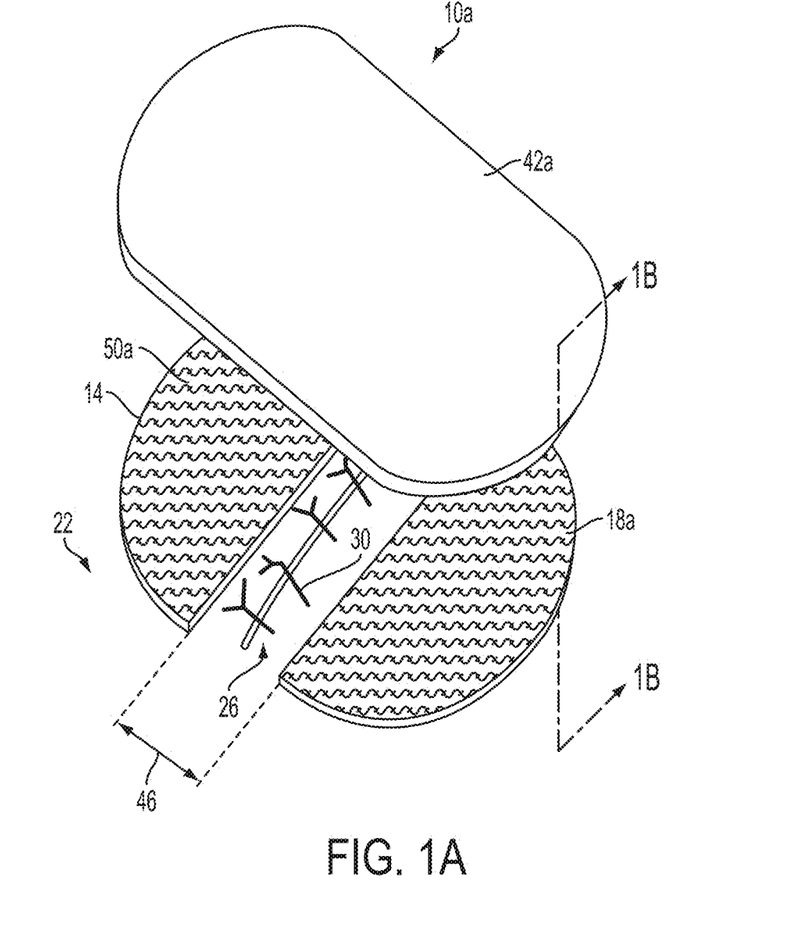
FIG. 1A is a top perspective view of a first embodiment of the present wound care apparatuses, shown in an open configuration.
Figure 1B:
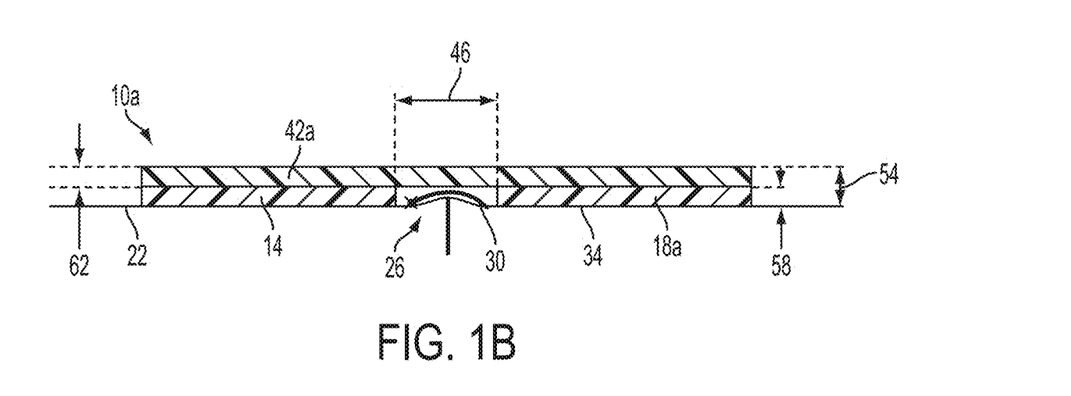
FIG. 1B is a cross-sectional side view of the embodiment of FIG. 1A, shown in a closed configuration.
Figure 2:
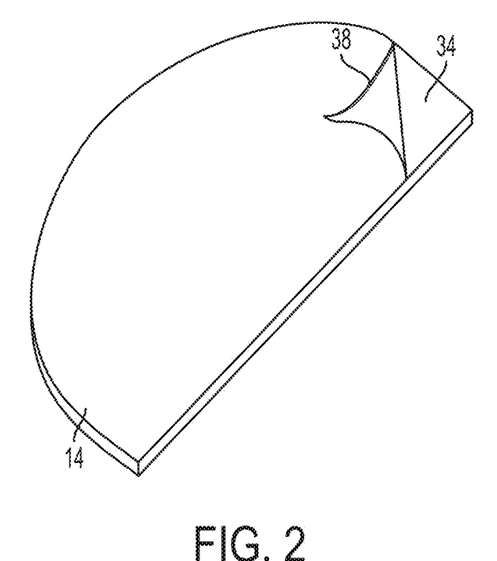
FIG. 2 is a bottom perspective view of a flexible strip of the embodiment of FIG. 1A.

Referring now to the drawings, and more particularly to FIGS. 1A, 1B, and 2, shown therein and designated by the reference numeral 10a is a first embodiment of the present wound care apparatuses. In the embodiment shown, apparatus 10a comprises a flexible first strip 14 and a flexible second strip 18a. For example, strips 14 and 18a are flexible in that they are configured to couple and contour to any suitable surface on a patient's body (e.g., as a patient ambulates and/or otherwise moves). For example, strips 14 and 18a can each comprise a synthetic cloth (e.g., nylon and/or the like), natural cloth (e.g., cotton and/or the like), plastic, and/or the like. As shown, apparatus 10a comprises two (2) flexible strips; however, other embodiments can comprise any suitable number of flexible strips, such as, for example, 2, 3, 4, 5, 6, 7, 8, 9, 10, or more flexible strips.

In this embodiment, strips 14 and 18a are configured to be coupled to a patient's skin (e.g., 22) on opposing sides of a wound (e.g., 26). As used in this disclosure, "wound" includes, but is not limited to, a cut, incision, opening, lesion, scar and/or the like, whether closed (e.g., with one or more sutures 30, as shown) or open.

For example, in the embodiment shown, strips 14 and 18a each comprise an adhesive backing 34 (FIG. 2) configured to be coupled to a patient's skin. In this embodiment, strips 14 and 18a each comprise a protective cover 38 configured to be coupled to and overlie at least a portion of adhesive backing 34. As shown, protective cover 38 can be removed from (e.g., peeled away) from the adhesive backing prior to use. In this way, adhesive backing 34 can be maintained in a sterile and/or tacky state and/or prevented from inadvertently adhering to surfaces before use. Adhesive backing 34 and/or protective covering 38 are provided only by way of example, as strips 14 and/or 18a can be configured to be coupled to a patient's skin through any suitable structure, such as, for example, glue, sutures, staples, and/or the like.

In the embodiment shown, apparatus 10a comprises a substantially inelastic and flexible layer of material 42a, such as, for example, comprising synthetic cloth (e.g., nylon and/or the like), natural cloth (e.g., cotton and/or the like), plastic, and/or the like. For example, in this embodiment, layer 42a is flexible such that it can be contoured to a surface of a patient's body and/or to portions of first strip 14 and/or second strip 18a; and layer 42a is also inelastic such that is will substantially resist stretching. In this way, when coupled to first and second strips 14 and 18a (e.g., in a closed configuration, shown in FIG. 1B), layer 42a is configured to prevent an increase of a maximum transverse distance 46 between (e.g., separation of) the first and second strips (e.g., by resisting an increase of distance 46 through tension). In the embodiment shown, maximum transverse distance 46 can be adjusted and/or set through relative placement of the first and second strips on the patient's skin and/or by displacing the patient's skin through relative movement of the first and second strips coupled to the patient's skin (e.g., prior to coupling layer 42a to the first and second strips). Maximum transverse distance 46 between first strip 14 and second strip 18a need not be uniform, and can vary along a wound (e.g., to vary puckering, compression, and/or the like applied to different portions of the wound).

To illustrate, a wound (e.g., 26) can be puckered and/or compressed by a clinician, strips 14 and/or 18a can be coupled to the patient's skin on opposing sides of the wound (e.g., if not already coupled to the patient), and layer 42a can be coupled to the strips, thus maintaining at least the puckering and/or compression set by the clinician. In this way, layer 42a can provide mechanical support for the wound and/or effectively increase the tensile strength of the wound. Thus, apparatus 10a may function to reduce loads (e.g., shear, tension, and/or the like) applied to the wound, for example, as a patient moves, thereby minimizing the risk of wound dehiscence, scar spreading, and/or the like.

In the embodiment shown, layer 42a, due in part its flexibility, is configured to generally permit a decrease in transverse distance between first strip 14 and second strip 18a (e.g., in a buckling and/or folding fashion). In this way, the wound and/or skin surrounding the wound is allowed a limited degree of movement, within the bounds of maximum transverse distance 46.

In this embodiment, layer of material 42a is configured to be directly coupled (e.g., without any intervening strips, layers, other components, and/or the like) to first strip 14 and second strip 18a (FIG. 1B). In this way, any tensile forces experienced by apparatus 10a can be substantially borne by layer 42a. In the embodiment shown, such direct coupling can be facilitated by engagement of hook-and-loop fasteners 50a, 50b (e.g., loops 50a and hooks 50b, collectively referred to as hook-and-loop fasteners FM) disposed on layer 42a and at least one of the first and second strips (e.g., both strips, in this embodiment). However, in other embodiments, such direct coupling can be accomplished through any suitable structure, such as, for example, adhesive, interlocking features disposed on layer 42a, first strip 14, second strip 18a, and/or the like. In some embodiments, described below, the layer may be non-removably coupled to and/or unitary with one or more flexible strip(s).

As shown, in this embodiment, one (1) layer 42a is configured to directly couple to and substantially overlie both first strip 14 and second strip 18a (e.g., to provide maximum mechanical support, wound coverage and/or protection, and/or the like). However, other embodiments can comprise any suitable number of layer(s), and the layer(s) can comprise any suitable size, shape, configuration, and/or the like, and need not be identical to one another. For example, in this embodiment, layer 42a, first strip 14, second strip 18a, and/or the like can be trimmed to any suitable shape (e.g., with scissors). Through size, shape, relative placement, configuration, and/or the like of the strip(s) and/or layer(s), the present wound care apparatuses can provide for varying degrees of airflow, applied tension, coverage, and/or the like to a wound, and these characteristics can be varied along the wound.

As illustrated by the depicted embodiment, the present wound care apparatuses can be configured to have a relatively slim profile, such that, for example, they can be discretely worn by a patient (e.g., under the patient's clothing). Such functionality can be achieved and/or facilitated by the direct coupling (e.g., lack of intervening strips, layers, other components, and/or the like) between layer 42a and strips 14 and 18a. For example, in this embodiment, apparatus 10a has a maximum thickness 54 that is substantially equal to a thickness 58 of the first and/or second strip plus a thickness 62 of the layer.

In the embodiment shown, layer 42a is configured to be removably coupled to at least one of first strip 14 and second strip 18a (e.g., in this embodiment, to each strip such that layer 42a can be completely decoupled from both strips). In the depicted embodiment, layer 42a can be removed from at least one of first strip 14 and second strip 18a without removing the strips from the patient's skin. For example, the strength of the direct coupling between layer 42a and strips 14 and/or 18a is sufficiently large to hold layer 42a under tension (as described above), but small enough to allow decoupling of layer 42a from the strips without overcoming the coupling between the strips and the patient's skin. In this way, layer 42a can be removed to access the wound to examine, clean, treat, and/or medicate the wound, and/or adjust the pucker and/or compression applied to the wound, and/or the like, without requiring reapplication or replacement of strips 14 and/or 18a.

In the depicted embodiment, layer 42a is configured to be recoupled to at least one of the first and second strips after the layer has been removed from the at least one strip (e.g., via hook-and-loop fasteners 50a, 50b, reusable adhesive, reapplication of adhesive, and/or the like). In this way, layer 42a can be removed to access the wound to examine, clean, treat, and/or medicate the wound, and/or adjust the pucker and/or compression applied to the wound, and/or the like as necessary (e.g., as wound healing progresses), without requiring replacement of layer 42a and/or strips 14 and/or 18a (e.g., layer 42a can be reapplied). However, in other embodiments, layer 42a may not be reusable (e.g., may be disposable) and/or can be replaced when desired (e.g., without removing or replacing the strips adhered to the patient's skin), for example, when the layer becomes contaminated (e.g., by body fluids, medicaments, and/or the like), damaged, and/or otherwise unsuitable for continued use).

Figure 3A:
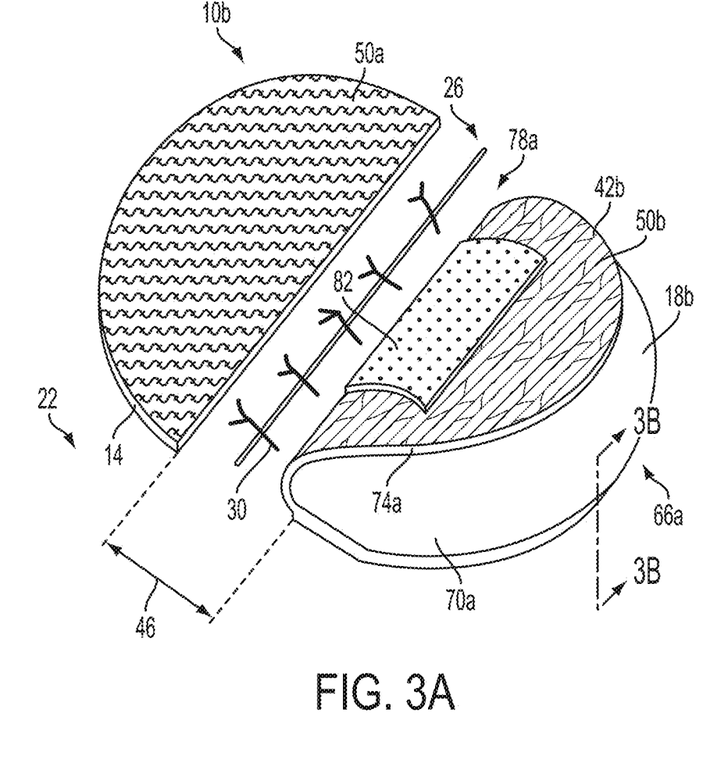
FIG. 3A is a top perspective view of a second embodiment of the present wound care apparatuses, shown in an open configuration.
Figure 3B:
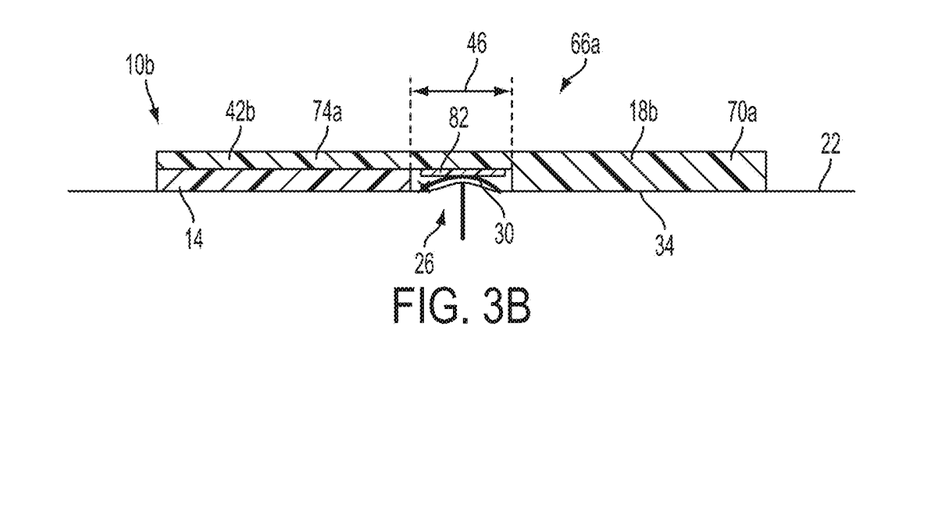
FIG. 3B is a cross-sectional side view of the embodiment of FIG. 3A, shown in a closed configuration.

FIGS. 3A and 3B depict a second embodiment 10b of the present wound care apparatuses. Apparatus 10b is substantially similar to apparatus 10a, with the primary exception that layer 42b of apparatus 10b is non-removably coupled to at least one of the first and second strips (e.g., second strip 18b). In the embodiment shown, layer 42b is unitary with (e.g., formed, at least in part, from the same piece of material as) strip 18b. For example, in this embodiment, layer 42b and strip 18b are defined by different portions of a single piece of flexible material 66a, for example, a portion 70a comprising an adhesive backing and an inelastic portion 74a, respectively. In other embodiments, the non-removable coupling of layer 42b and flexible strip 14 and/or 18b can be accomplished through any suitable structure, such as, for example, glue, stitching, and/or the like.

In the embodiment shown, a proximal surface of second strip 18b (e.g., portion 70a) can comprise a releasable coupler (e.g., hook-and-loop fasteners, adhesive, interlocking features, and/or the like) configured to retain layer 42b (e.g., portion 74a) in an open configuration, where layer 42b is not coupled to strip 14 (e.g., such that portion 74a overlies a portion of portion 70a, as shown). In this embodiment, layer 42b, strip 18b, and/or flexible material 66a, when in the open position, define a folded edge 78a that is configured to face generally towards a wound (e.g., 26).

In the embodiment shown, layer 42b comprises an absorbent pad 82. Absorbent pad 82 can be included in any and/or all embodiments of the present wound care apparatuses. Absorbent pad 82 can be configured to absorb and/or retain fluids (e.g., medicaments, body fluids, and/or the like), facilitate protection of a wound (e.g., 26), and/or enhance patient comfort (e.g., by cushioning any interface between layer 42b and the wound). In some embodiments, absorbent pad 82 may be replaceable (e.g., to facilitate reusability of layer 42b).

Figure 4A:
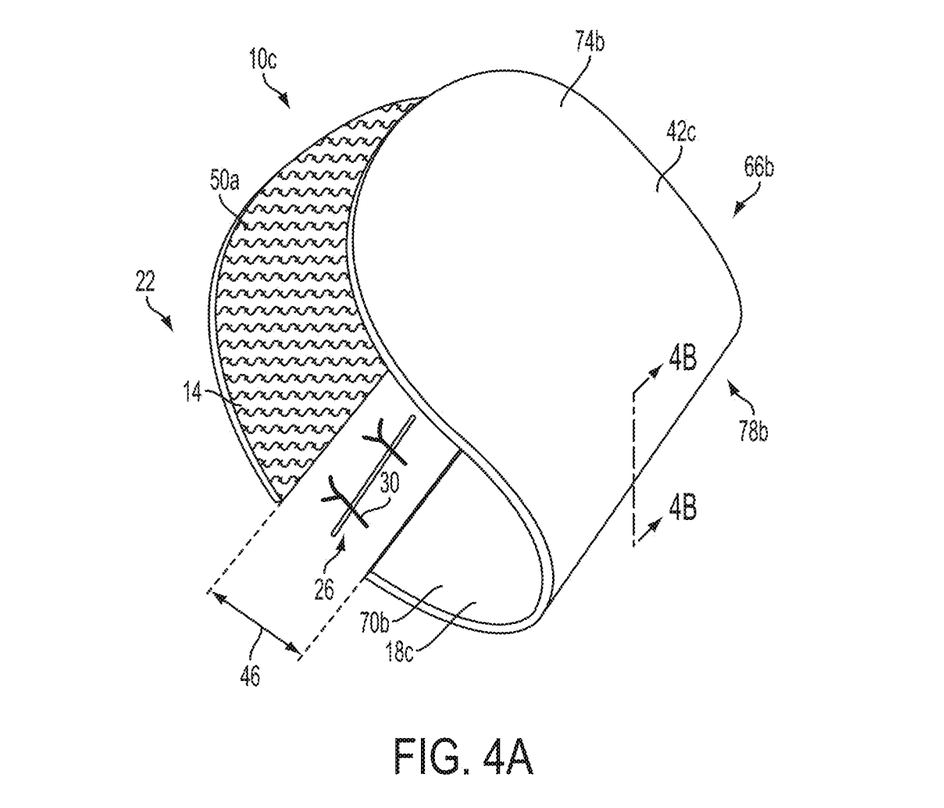
FIG. 4A is a top perspective view of a third embodiment of the present wound care apparatuses, shown in a partially closed configuration.
Figure 4B:
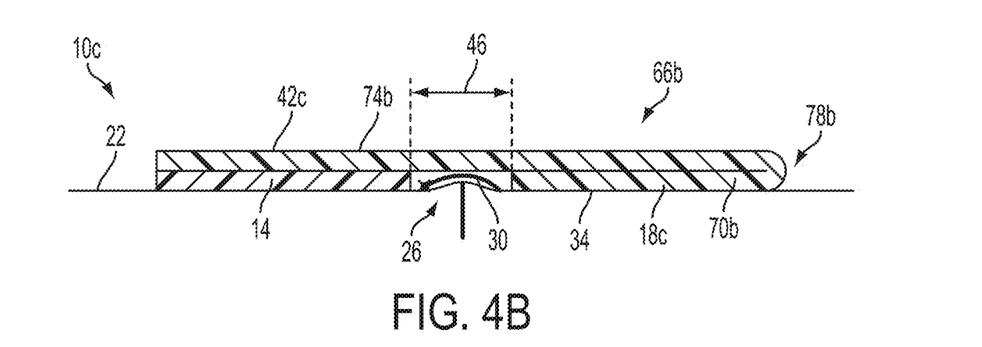
FIG. 4B is a cross-sectional side view of the embodiment of FIG. 4A, shown in a closed configuration.

FIGS. 4A and 4B depict a third embodiment 10c of the present wound care apparatuses. Apparatus 10c is substantially similar to apparatus 10b, with the primary exception that layer 42c, strip 18c, and/or flexible material 66b of apparatus 10c, when in the closed position, define a folded edge 78b configured to face generally away from a wound (e.g., 26). In this embodiment, a proximal surface of strip 18c (e.g., portion 70b) can comprise a releasable coupler (e.g., hook-and-loop fasteners, adhesive, interlocking features, and/or the like) configured to retain layer 42c (e.g., portion 74b) in a generally closed configuration, where layer 42c is coupled to strip 14 (e.g., such that portion 74b overlies a portion of portion 70b, as shown).

Some embodiments of the present methods for minimizing scar spread and reducing risk of wound dehiscence comprise coupling a first flexible strip (e.g., 14) and a second flexible strip (e.g., 18a, 18b, 18c, and/or the like) to a patient's skin (e.g., 22) on opposing sides of wound (e.g., 26), and coupling a substantially inelastic and flexible layer (e.g., 42a, 42b, 42c, and/or the like) across the first and second strips such that the layer is held in tension by the first and second strips. In some methods, the layer is directly and removably coupled to at least one of the first and second strips. Some methods comprise removing the layer from at least one of the first and second strips without removing the first and second strips. Some methods comprise recoupling the layer across the first and second strips such that the layer is held in tension by and resists separation of the first and second strips. Some methods comprise applying a medicament to the wound. Some embodiments comprise trimming at least one of the first strip, second strip, and/or layer.

Some embodiments of the present methods for minimizing scar spread and reducing risk of wound dehiscence comprise adjusting a distance (e.g., 46) between a flexible first strip and a flexible second strip, the first and second strips coupled to a patient's skin on opposing sides of a wound; and coupling an inelastic and flexible layer of material across the first and second strips such that the layer is held in tension by and resists separation of the first and second strips.

In some methods, at least a portion of the wound is on the patient's back. In some methods, at least a portion of the wound is on the patient's thigh.

Some embodiments of the present methods for providing access to a wound comprise releasing a substantially inelastic and flexible layer of material from a direct coupling with at least one of a first flexible strip and a flexible second strip in which the layer is under tension between the first and second strips, where the first and second strips remain coupled to a patient's skin on opposing sides of the wound.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method for minimizing scar spread and reducing risk of wound dehiscence, the method comprising:
   coupling a flexible first strip and a flexible second strip to a patient's skin on opposing sides of a sutured wound; and
   coupling a substantially inelastic and flexible, substantially planar layer of material across the first and second strips such that the layer overlies at least a portion of each of, and is held in tension by, the first and second strips and such that the layer overlies substantially all of at least one of the first and second strips;
   where the layer is non-removably coupled to one of-the first and second strips.

2. The method of claim 1, where the layer is directly and removably coupled to at least one of the first and second strips.

3. The method of claim 2, where coupling the layer across the first strip and second strip comprises covering substantially all of the second strip with the layer.

4. The method of claim 1, comprising removing the layer from at least one of the first and second strips without removing the first and second strips from the patient's skin.

5. The method of claim 4, comprising recoupling the layer across the first and second strips such that the layer is held in tension by and resists separation of the first and second strips.

6. The method of claim 4, where the layer is directly and non-removably coupled to the first strip.

7. The method of claim 1, comprising applying a medicament to the sutured wound.

8. The method of claim 1, comprising trimming at least one of the first strip, second strip, and layer.

9. The method of claim 1, where coupling the layer across the first strip and second strip comprises covering substantially all of the first strip with the layer.

10. The method of claim 1, where the layer is directly and non-removably coupled to the first strip.

11. The method of claim 10, further comprising:
creating a folded edge between the first strip and the layer;
where coupling the layer across the first and second strips comprises:
coupling the layer such that a side of the first strip positioned between the sutured wound and the folded edge is also positioned between the layer and the patient's skin; and
covering at least a portion of the second strip.

12. The method of claim 1, where:
the layer has a first thickness, the first strap has a second thickness, and the second strip has a third thickness; and
the second thickness of the first strip is approximately the same as the first thickness of the layer, the third thickness of the second strip, or both.

13. The method of claim 1, further comprising contacting an absorbent pad to the sutured wound.

14. The method of claim 13, where
the absorbent pad is coupled to the layer;
the absorbent pad has a width smaller than a distance between the first strip and the second strip; and
a thickness of the absorbent pad is less than a thickness of the first strip, a thickness of the second strip, or both.

15. The method of claim 1, where in the substantially inelastic and flexible, substantially planar layer of material comprises a single substantially inelastic and flexible, substantially planar layer of material.

16. A method for providing access to a sutured wound, the method comprising:
releasing a substantially inelastic and flexible, substantially planar layer of material from a direct coupling with one of a flexible first strip and a flexible second strip in which the layer is under tension between the first and second strips;
where the first and second strips remain coupled to a patient's skin on opposing sides of the sutured wound; and
where the layer overlies substantially all of at least one of the first and second strips.

17. The method of claim 16, comprising applying a medicament to the sutured wound.

18. A method for minimizing scar spread and reducing risk of wound dehiscence, the method comprising:
adjusting a distance between a flexible first strip and a flexible second strip, the first and second strips coupled to a patient's skin on opposing sides of a sutured wound; and
coupling an inelastic and flexible layer of material across the first and second strips such that the layer is held in tension by and resists separation of the first and second strips;
where the layer is configured to substantially overlie both of the first and second strips.

19. The method of claim 18, where coupling of the layer to at least one of the first and second strips is removable and direct.

* * * * *

UNITED STATES PATENT AND TRADEMARK OFFICE
CERTIFICATE OF CORRECTION

PATENT NO.        : 10,596,041 B2  
APPLICATION NO.   : 14/663833  
DATED             : March 24, 2020  
INVENTOR(S)       : James Allred Page 1 of 1

It is certified that error appears in the above-identified patent and that said Letters Patent is hereby corrected as shown below:

On the Title Page (71) Applicant:
Delete "SETON HEALTHCARE FAMILY" and replace with -- ASCENSION TEXAS --.

Signed and Sealed this
Tenth Day of November, 2020

Andrei Iancu
*Director of the United States Patent and Trademark Office*